United States Patent
Lotfi (12)

(10) Patent No.: US 6,491,624 B1
(45) Date of Patent: Dec. 10, 2002

(54) DEVICE FOR PEROPERATIVE EXPLORATION OF A CARDIOVASCULAR SYSTEM

(76) Inventor: Houari Lotfi, 38 rue de Touraine, 49100 Angers (FR)

( * ) Notice: Subject to any disclaimer, the term of this patent is extended or adjusted under 35 U.S.C. 154(b) by 0 days.

(21) Appl. No.: 09/647,949

(22) PCT Filed: Apr. 6, 1999

(86) PCT No.: PCT/FR99/00790

§ 371 (c)(1),
(2), (4) Date: Nov. 20, 2000

(87) PCT Pub. No.: WO99/51169

PCT Pub. Date: Oct. 14, 1999

(30) Foreign Application Priority Data

Apr. 6, 1998 (FR) ............................................. 98 04220
Jun. 29, 1998 (FR) ............................................. 98 08370
Oct. 5, 1998 (FR) ............................................. 98 12466

(51) Int. Cl.[7] ................................................. A61F 2/24
(52) U.S. Cl. ........................ 600/114; 600/109; 600/160; 623/921; 623/922
(58) Field of Search ................................ 128/898, 899; 600/101, 109, 114, 160; 623/913, 921, 922

(56) References Cited

U.S. PATENT DOCUMENTS 3,548,418 A * 12/1970 Angell et al. .............. 623/2.17
5,163,955 A * 11/1992 Love et al. .................. 623/900
5,406,857 A * 4/1995 Eberhardt et al. ............. 73/37
5,571,215 A * 11/1996 Sterman et al. ............. 128/898
5,861,028 A * 1/1999 Angell ........................ 623/900
5,972,020 A * 10/1999 Carpentier et al. .......... 600/114

FOREIGN PATENT DOCUMENTS

WO  WO-A-92 12690  * 8/1992
WO  WO-A-97 25004  * 7/1997

* cited by examiner

Primary Examiner—John Rivell
Assistant Examiner—Ramesh Krishnamurthy
(74) Attorney, Agent, or Firm—Young & Thomspon

(57) ABSTRACT

A device for exploration of the cardiovascular system of human or animal bodies includes a generally transparent blind tube delimiting a cavity in which can be disposed an optical display device, the open end of the tube being shaped to be ensleeved axially in a sealed manner in the passage of an artery or of a vein having first been at least partially sectioned such that the cavity of the tube in the interior of the artery or of the vein form a common chamber at least partially closeable by a cardiac valve. The tube, maintained in ensleeved position by a suitable securement member, includes at least one supplemental opening for the introduction into the cavity of the tube of a physiological liquid under pressure.

11 Claims, 4 Drawing Sheets

DEVICE FOR PEROPERATIVE EXPLORATION OF A CARDIOVASCULAR SYSTEM

BACKGROUND OF THE INVENTION

The present invention relates to a device for the per-operative exploration of organs such as veins or arteries or ventricles, of the cardiovascular system of human or animal bodies, in particular to determine the state of functionality of the cardiac valves or valvules.

The most serious operations, because of their consequences for the rest of the human or animal body, require a systematic control of the quantity of surgical intervention. Thus, in the case of cardiac interventions, after aortaplasty or replacement of the aortic valve by a homograft, a pulmonary autograft or a heterograft without a prop, it is necessary, to appreciate the quality of the surgical work, to provide a transesophagal echograph (TOE) after reclosing the aortotomy and stopping the extracorporeal circulation (ECC). Because of this, when there is detected an imperfection in the work of the surgeon, it is necessary to provide a new aortotomy and to replace an ECC device.

SUMMARY OF THE INVENTION

The object of the present invention is thus to provide a device for per-operative exploration of veins, arteries or ventricles of the cardiovascular system of human or animal bodies, which permits appreciating, at any moment during the procedure, the quality of the work carried out by the surgeon.

Another object of the present invention is to provide a device for per-operative exploration of veins or arteries or ventricles of the cardiovascular system of the human or animal body, whose design permits testing the sealing of the valvuloplasties, of the prostheses, of the native valves, to appreciate the quality of the coaptation of the sigmoids and to detect and analyze an imperfection of a prop so as to remedy it immediately.

To this end, the invention has for its object a device for per-operative exploration of organs, such as veins or arteries, in particular of the aorta or ventricles, of the cardiovascular system of the human or animal body, in particular to appreciate the condition of operation of the cardiac valves, or the valvules, or the stents, or the prosthetic tubes, characterized in that it is constituted by an elongated hollow body, such as a tube, made of a sealed material, preferably transparent, said body delimiting a cavity in which can be disposed, permanently or temporarily, optical display means, such as a camera, said cavity being open into and/or into the vicinity of, one end of the hollow body, this open end of the hollow body, adapted to be introduced through an opening of the organ to be explored, being shaped to be able, directly or by means of at least one suitable securement member, to connect, in a substantially sealed manner, the body to the organ, such that the cavity of the hollow body and the interior of the organ form a common chamber at least partially closeable by a cardiac valve, a valvual and/or by a closure member provided in the organ, this hollow body comprising, preferably opposite the open end of the body, at least one supplemental opening opening into said cavity of the body for the introduction into said cavity of the hollow body a liquid under pressure permitting, in the condition introduced into the body in an organ, an increase of the pressure prevailing within the organ so as to facilitate the possible functional exploration of it.

Thanks to this design of the device, it is possible, at any moment during the intervention and in several seconds, to verify the quality of the work of the surgeon, to test the possible sealing of the cardiac valves, or the valvules, the position of the valves, or of the valvules, by the naked eye.

Moreover, because of this design, such a device does not necessarily require, for the surgeon, to modify the aortotomy as it is conventionally practiced. Thus, in the case in which the aorta is at least partially sectioned, the hollow body is simply ensleeved axially within the arterial passage or the vein.

According to a first preferred embodiment of the invention, the hollow body comprises, over its periphery, in the region for connection to an organ to be explored, at least one continuous or discontinuous external circumferential swelling and/or recess, arranged to form respectively at least one portion of a swelling or trough, which swelling and/or trough coact with the securement member of the device to ensure a connection, in particular a sealed ensleeving of the body in the organ to be explored and to prevent any sliding of the body out of the organ to be explored.

According to a second embodiment of the invention, the hollow body comprises over its periphery a ring mounted slidably on said body to come, when the open end of the hollow body is introduced through an opening of a ventricle within this latter, to bear against the external periphery of the opening provided in the ventricle and to ensure, in cooperation with the walls of the ventricle, a substantially sealed connection between the hollow body and the ventricle.

BRIEF DESCRIPTION OF THE DRAWINGS

The invention will be better understood from a reading of the following description of examples of embodiment, with reference to the accompanying drawings, in which.

DESCRIPTION OF THE PREFERRED EMBODIMENTS

Figure 1:
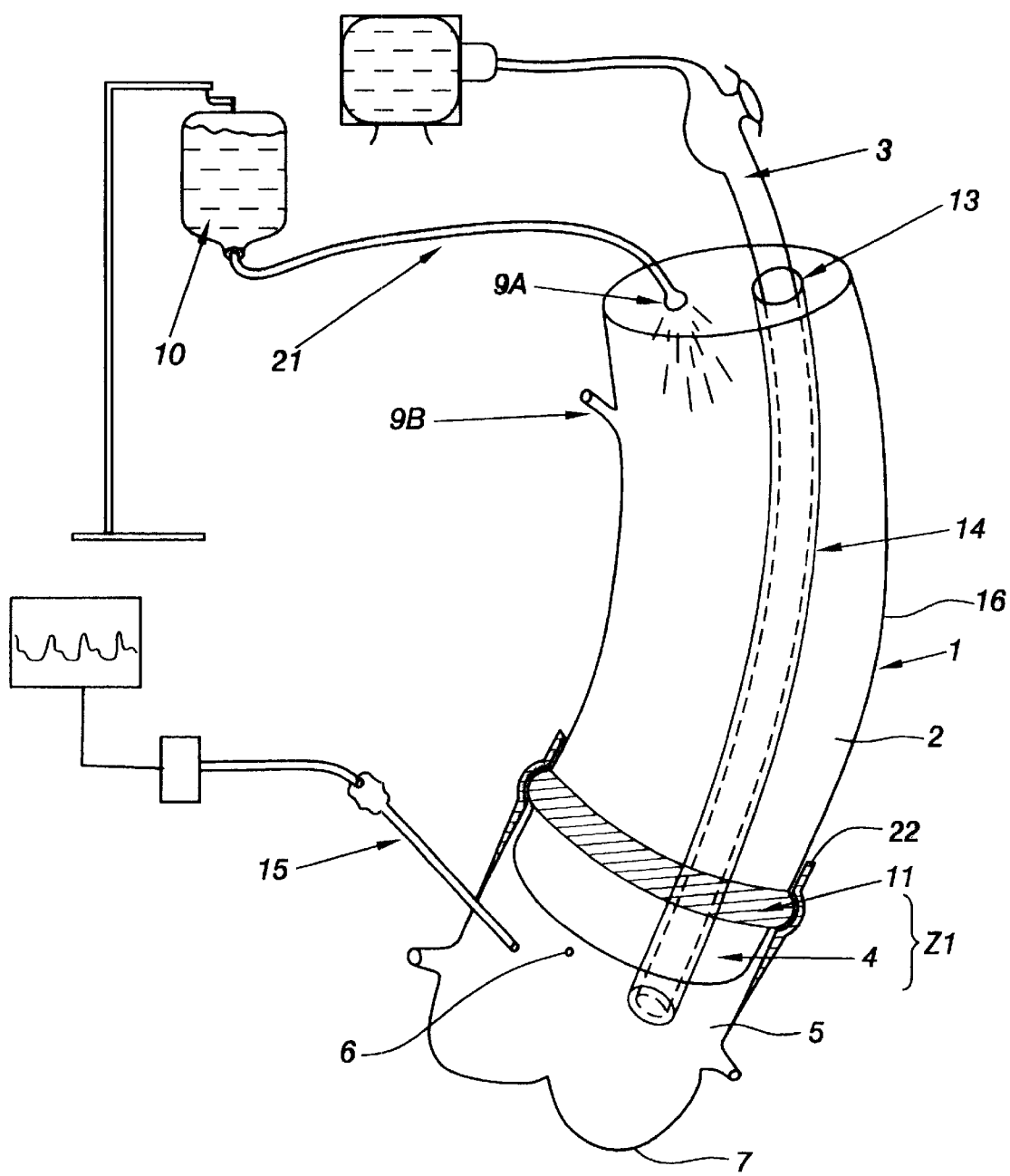
FIG. 1 shows a schematic perspective view of the device, which is the object of the invention, in a position installed on an artery constituted by the aorta.

The exploration device, according to the invention, is a per-operative exploration device permitting at any time, in the course of a surgical intervention, to explore the veins, the arteries, in particular the aorta, or the ventricles, of the cardiovascular system of the human or animal body and to determine in particular the state of operation of the cardiac valves, the valvules, or the condition of stents, or of prosthetic tubes, positioned in the arteries.

More and more, surgical operations carried out are complex operations. Such surgical interventions, in particular the aortaplasties, require immediately being able to control the effectiveness and the sealing of this plasty to as to obtain the best results. It is thus necessary to be able to test the sealing of the valvular replacement whether in the pericardium, with a homograft, a heterograft, a biological or mechanical prosthesis, the pressure which acts directly on the aortic valves in the closed position, the position of the valves to the naked eye, etc. The per-operative exploration device according to the invention permits such tests. In the examples of embodiments described below, this device will be more particularly described in the field of its introduction into the veins or arteries. However, it may similarly be introduced into a ventricle of the heart.

To do this, this exploration device is constituted by an elongated hollow body 1, such as a tube, made of a sealed material, generally transparent and preferably semirigid. Generally, the device comprises means 15 for measuring the pressure prevailing within a chamber 6 common to the hollow body cavity 1 and to the interior of the organ 5 to be explored, to determine the quantity of liquid 10 to be introduced into this chamber 6 so as to obtain, within this chamber 6, a physiologically acceptable pressure. This body 1 defines a closed cavity 2 in which can be disposed, permanently or temporarily, optical display means 3, such as a camera. This cavity 2 is open to, or into the vicinity of, an end of the hollow body 1 thanks to lateral openings (not shown) or axial openings 4 provided at the end of this body 1. This open end 4 of the hollow body 1 is shaped to be introduced through an opening 22 provided in the organ to be explored. This opening 22 in the organ can be provided by sectioning at least partially the artery or the vein such that the open end 4 of the body 1 is thus ensleeved axially within the passage of the organ and connected sealingly to this latter. In this case, on the contrary, in which the vein or the artery, and particularly the aorta, has an incision provided on its lateral wall, the open end of the body is introduced radially into the artery or the vein before being connected in a sealed manner to this latter. Thus, in the case of the example shown in FIG. 1, the artery 5 in which will be ensleeved the hollow body 1, is the aorta. Because of its design, the device according to the invention does not require the surgeon to modify his work during practice of the aortotomy. Thus, in the case for example of a cardiac intervention on the aortic valve, the aortotomy practiced is a circumferential anterior aortotomy sparing the rear surface of the aorta. The device according to the invention permits respecting this aortotomy.

In its simplest version, the body 1 is constituted by a simple tube of the semi-rigid test tube type, generally cylindrical, if desired elbowed, open at or near one end and closed at its other end. When the end of the body is sufficiently introduced into the artery, or the vein, or the ventricle, which is to say beyond the openings of the cavity, the cavity of the body 1 and the interior of the organ 5 form a common chamber 6. According to the emplacement at which has been provided the sectioning or an incision of the organ, this common chamber can be partially closeable by a cardiac valve 7, by a valvule and/or by at least one closure member provided in the organ. In this case, this closure member constitutes one of the elements of the device. This closure member can be constituted by a clamp or by a simple balloon disposed in the artery or in the vein downstream of the section of the artery or of the vein to be observed taken in the direction of introduction of the body into the artery or the vein.

In the example shown in the figures, this common chamber 6 is closed by the aortic valve 7, the object being in this case to verify the operation of this latter.

Figure 3:
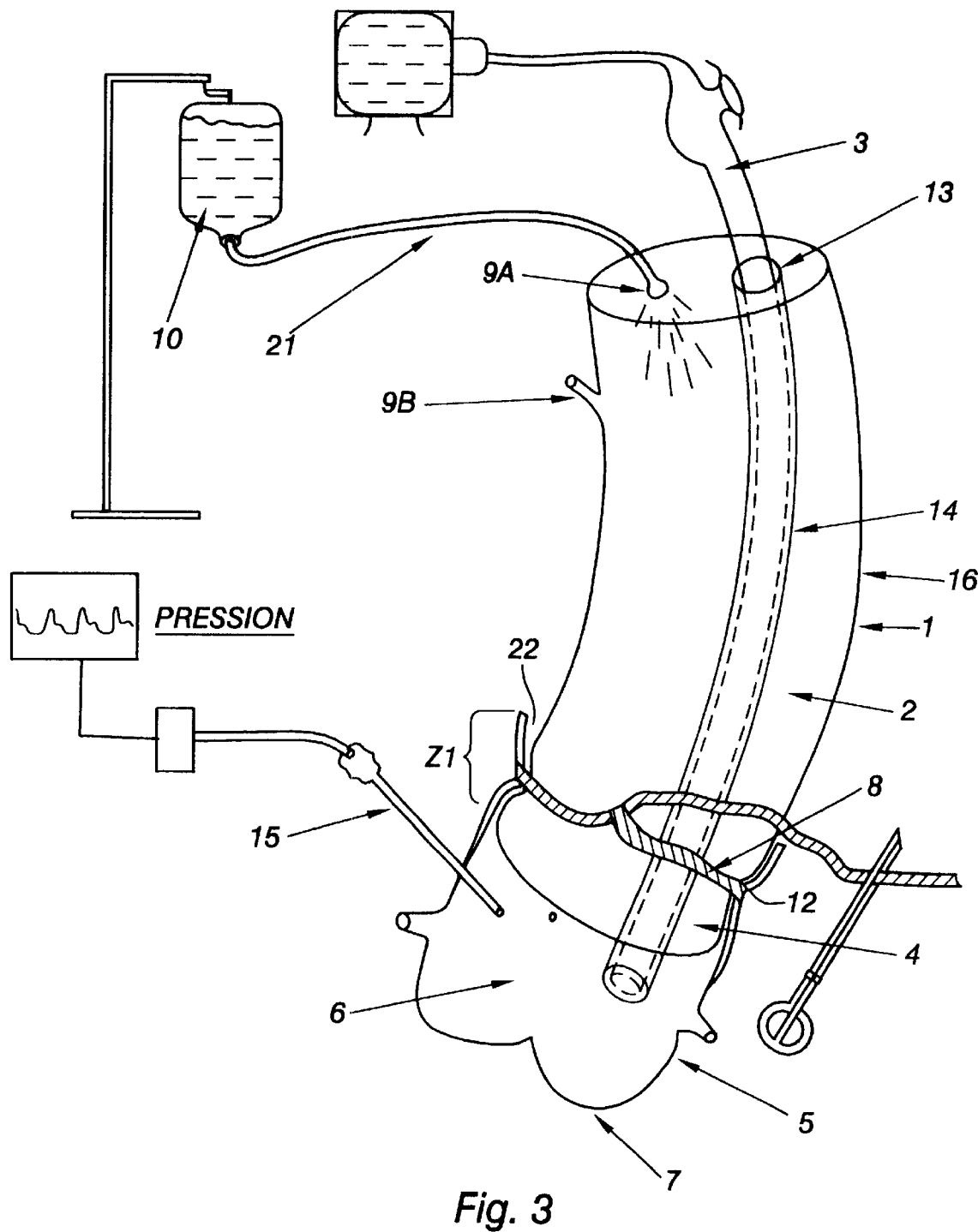
FIG. 3 shows a perspective view of another embodiment of the device.

The hollow body 1 is maintained in substantially sealed connected position in the organ 5 by means of a securement member 6, such as a member pressing at least a portion of the walls of the organ 5 against the sidewalls of the hollow body 1. To guarantee the solidity and sealing of this connection, the hollow body 1 comprises about its periphery, in its region Z1 of connection in an organ 5, at least one continuous or discontinuous external circumferential swelling 11 or recess 12 arranged to form respectively at least one portion of an enlargement or a trough, which enlargement and/or trough coact with the securement member 8 of the device to ensure a connection, in particular a sealed ensleeving of the body 2 in the organ 5 and to prevent any sliding of the body 2 out of the organ 5. Thus, in the example shown in FIG. 1, the hollow body 1 comprises over its periphery a continuous external circumferential swelling 11. This swelling 11 can be provided by at least one ring connected to the body or made of a single piece with said hollow body 1. Conversely, in the example shown in FIG. 3, the hollow body 1 comprises about its periphery a continuous external circumferential recess 12 providing a trough about said body 1. Generally, in the case of a continuous recess, this recess has a width of about 3 mm and occupies a third of the thickness of the wall of the hollow body 1. In the other solution consisting in connecting for example a cylindrical ring to provide a circumferential external swelling about the periphery of the hollow body 1, there will be preferably selected a ring transparent to radiation. It is also possible to combine the two solutions. In this case, the hollow body 1 comprises, adjacent its free end, a continuous circumferential recess adapted to receive a cylindrical ring whose external surface is of a shape complementary to that of the recess. This ring will in this case preferably have a rigid consistency, and be non-slip and atraumatic. The choice of the swelling or the recess will be a function of the physical characteristics of the organ of the patient.

Figure 4:
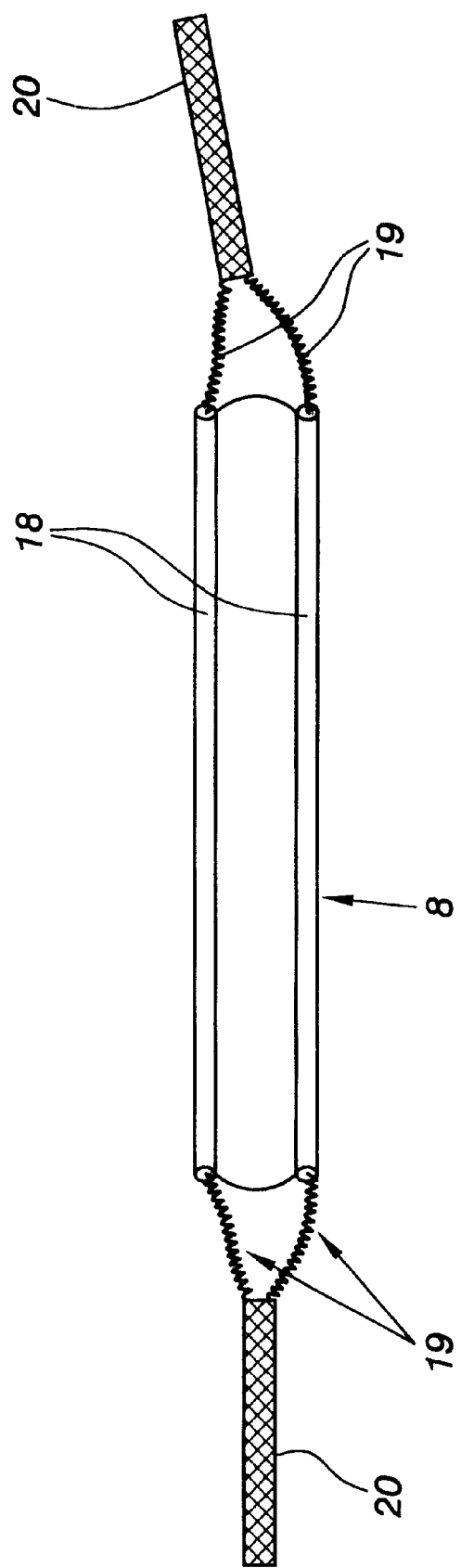
FIG. 4 shows a bottom view of a securement member of the device to an artery.

The securement member 8 used to ensure the maintenance of this connection can be of any shape. Thus, the securement member 8 of the organ 5 to the body 1 can have the shape of a resiliently deformable open ring. This securement member 8 of the organ 5 to the body 1 can also have the shape of a belt, as shown in FIG. 4. This belt can thus, by way of example, be constituted by a woven strip of substantially rectangular shape. The internal surface of this belt has a concavity over all its length. Each of the two free longitudinal edges 18 of this belt is folded back on itself to delimit a sleeve within which is introduced a cord 19. At the free ends of the cord 19 is secured a woven strip 20, generally self-gripping. This belt also comprises on its back a self-gripping strip adapted to coact with self-gripping strips 20 disposed in prolongation of the ends of the cord 19 to permit, after positioning the belt about the walls of the organ and tightening the cord, a holding in position of this latter. The concavity of the belt permits matching perfectly the swelling of the hollow body 1 when this swelling exists. Such a belt shows the advantage of being able to be fixed in several seconds about the organ and to ensure, in spite of everything, good sealing of the connection. Another example of securement member 8 has also been shown in FIG. 3. In this case, this securement member is constituted by a simple periaortic lace. Finally, it is to be noted that other securement members permitting connection by screwing or the like can be used. Furthermore, in the case in which the body 1 is introduced through an opening provided in the ventricle, a securement member is not necessary to ensure a substantially sealed connection between the body and the ventricle because the natural construction of the walls of the ventricle can ensure this sealing.

The hollow body 1 also comprises at least one supplemental opening 9A, 9B opening into said cavity 2 of the body 1 for the introduction into said cavity of the hollow body 1 of a liquid 10 under pressure permitting an increase of the pressure prevailing within the organ 5 so as to facilitate the possible desired functional operation of it.

Thus, in the example shown in FIG. 1, a pressure body contains a liquid 10 under pressure, this liquid being adapted to be constituted for example by a serum or cardioplegic liquid. A flexible conduit 21 serves as a connection conduit between the open end of this liquid pocket under pressure and the opening 9A of the hollow body 1. Obviously, the openings 9A, 9B can have various shapes as a function of the shape of the connection conduit. In particular, the edges of these openings 9A, 9B can project outside the body 1.

Generally speaking, the hollow body 1 comprises at least two openings 9A and 9B for the introduction of a liquid under pressure into the cavity 2 of the body 1. At least one of the openings is provided on a side wall of the body 1 so as to permit the use of the device in particular for young patients. Moreover, the openings 9A and 9B comprise closure members (not shown). It is to be noted that one of the openings can also be used for the connection of the body, and in particular of the cavity of the body, to a suction device.

Figure 2:
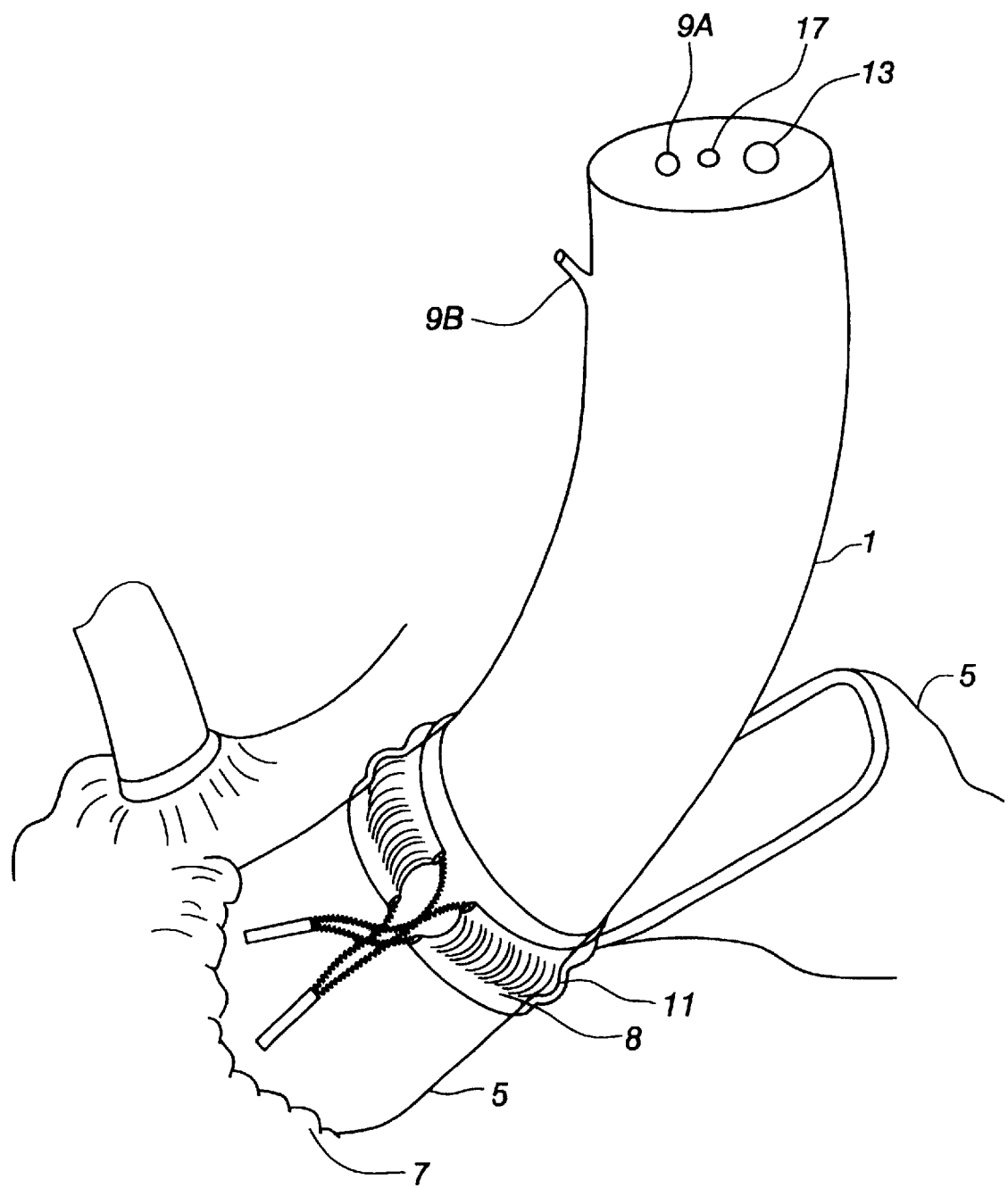
FIG. 2 shows another perspective view of the device, according to the invention, in a fixed position in a sealed manner on the aorta.

The device also comprises means 15 for measuring the pressure prevailing within said common chamber 6 to determine the quantity of liquid 10 to be introduced into this chamber 6 so as to obtain, within said chamber 6, a physiologically acceptable pressure. Generally speaking, these means 15 are constituted by a manometer connected to a probe. In a particular embodiment of the invention, the probe of the means 15 for measuring the pressure is introduced into the hollow body 1 through a supplemental opening 17 provided in or adjacent the upper end of said hollow body 1, as shown in FIG. 2.

The optical display means 3 can themselves be single use means positioned in the cavity 2 of the hollow body 1, adjacent the open end 4 of the body 1, during production of said body 1. These means are thus constituted by a camera orientable by means of an arm projecting outside said body.

In another embodiment of the optical display means 3, such as shown in FIG. 1, the hollow body comprises a supplemental opening 13 whose edges are secured to a generally flexible pocket 14 by partially transparent means shaped to be able to be disposed within the cavity 2 of said body 1. This at least partially transparent generally flexible pocket 14 serves for the reception of optical display means 3, such as a camera or a fibroscope, and isolates said display means 3 from the rest of the contents of said cavity 2 of the hollow body 1. It is thus possible to reuse the optical display means.

To use such a device, one proceeds for example in the following manner. The surgeon measures in a first step the internal diameter of the organ which must be explored. He then selects a hollow body 1 whose external diameter is substantially equivalent to that of the organ. The open end of the hollow body is introduced within the organ, for example the aorta, as in FIG. 1. Generally speaking, when the selected organ is the aorta, the hollow body 1 is positioned on the aortic artery 5, such that the connection zone of the open end 4 of the hollow body 1 to the aorta is provided in the sinotubular region of the ascending aorta. This is according to the example shown in FIG. 1.

Aortotomy is carried out as is conventional for such operations. The results of this aortotomy are more particularly visible in FIG. 2. The open end 4 of the hollow body 1 is introduced into the passage of the aorta such that the aorta receives a swelling or a recess of the hollow body when this latter exists and extends substantially above this swelling or this recess, this excess being generally of the order of 4 mm.

Once the hollow body 1 is positioned in the passage of the organ to be explored, the securement member 8 is secured. After securement and gripping of this securement member, a source of liquid 10 under pressure is connected for example through to the opening 9B located on the lateral surface of the hollow body thanks to a tube 21. A probe of the pressure manometer 15 is introduced through a second opening 17 of the hollow body 1 or directly into the root of the organ to be explored. At the same time, optical display means are emplaced, in particular a camera or a fibroscope, through the third opening 13 of the hollow body 1 such that these optical means extend within the flexible pocket 14. The injection of fluid 10 into the common chamber 6 can then commence. This injection is provided such that the flow rate is progressively increased. Thanks to the images taken in real time by the optical display means and if desired to the transparency of the body, it becomes easy to oversee the flow of the liquid, the position of the fibroscope and the movements of the artificial valve flaps or of the natural valves. At the same time, thanks to the external pressure manometer, it is easy to oversee the intra-aortic pressure which simulates the physiological diastolic pressure. Because of the ease of mounting and unmounting the device, this operation of controlling, exploring and testing can be carried out several times until a sealing is obtained conforming to a natural functioning of the valves. Such a device thus permits overcoming immediately small faults of suturing, of repair, of mounting, and preventing any postoperative aortic leakage, etc. Moreover, such a device permits, on natural valves, to survey perfectly the closure of the sigmoids and then the stretching of the Valsalva sinuses, to the extent that the pressure increases and, finally, the coaptation of the aortic sigmoids and of the mitral, tricuspid and pulmonary valves.

It is to be noted that, to carry out a complete exploration, it will sometimes be necessary to visualize simultaneously also the ventricular surface of the aortic valve, this visualization taking place simply by means of a fibroscope introduced into the point of the left ventricle. Similarly, for damaged valves, the device permits taking account of the absence of the tensioning of the Valsalva sinuses because of a leakage which can be perfectly localized when a fibroscope is introduced into the point of the left ventricle. Finally, for repaired valves, the qualities and defects of the different mountings can be appreciated.

What is claimed is:

1. A device for the per-operative exploration of an organ of a cardiovascular system of a human or animal body, comprising:

a hollow body made of a sealed material, said hollow body defining a cavity for an optical display device, said cavity being open into and/or into the vicinity of an open end of the hollow body, the open end of the hollow body being introduced through an opening of an organ to be explored and being shaped to directly or by means of at least one suitable securement member to connect in a substantially sealed manner the hollow body to the organ such that the cavity of the hollow body and an interior of the organ to be explored form a common chamber at least partially closeable by a closure member present in the organ to be explored, the hollow body comprising, opposite the open end of the hollow body, at least one supplemental opening that opens into said cavity for the introduction into said cavity of a liquid under pressure to increase a pressure prevailing within the organ so as to facilitate the exploration.

2. The exploration device according to claim 1,
wherein the hollow body comprises, over its periphery, in its region of connection to the organ to be explored, at least one continuous or discontinuous external circumferential swelling and/or recess to form respectively at least one enlarged or recessed portion, which enlargement and/or recess coacts with the securement member to ensure a sealed ensleeving of the hollow body in the organ to be explored.

3. The device according to claim 1,
wherein the securement member presses on at least a portion of walls of the organ to be explored against sidewalls of the hollow body.

4. The exploration device according to claim 3,
wherein the securement member is shaped as an elastically deformable open ring or a belt.

5. The exploration device according to claim 1,
wherein the hollow body comprises, at its periphery, a ring slidably mounted on the hollow body the ring being applied against an external periphery of an opening in a ventricle and ensuring, in coaction with a ventricle wall, a substantially sealed connection between the hollow body and the ventricle.

6. The exploration device according to claim 1,
wherein the hollow body comprises a further supplemental opening whose edges are secured to a pocket at least partially transparent and shaped to be able to be disposed within the cavity, this at least partially transparent pocket serving for the reception of the optical display device, and isolating said display device from other contents of said cavity.

7. The exploration device according to claim 1,
wherein the optical display device comprises a camera orientable by means of an arm projecting outside said body.

8. The exploration device according to claim 1,
wherein said body comprises at least two of said supplemental opening, at least one of the supplemental openings being provided on a lateral wall of the body, said supplemental openings comprising closure members.

9. The exploration device according to claim 1,
further comprising means for measuring the pressure prevailing within said common chamber to determine a quantity of liquid to be introduced into said chamber.

10. The exploration device according to claim 1,
wherein the hollow body comprises at least one elbow.

11. A device for per-operative exploration of an organ of a human or animal body, the device comprising:
 a hollow body defining a cavity, an open end of said cavity being adapted to be placed, using a connection device, into an opening of an organ to be explored so that an interior of the organ and the cavity form a common chamber,
 the connection device including a securement member placed so as to connect the hollow body and the organ in a substantially sealed manner,
 the hollow body comprising at least one supplemental opening opposite to the open end for introducing a liquid under pressure into an interior of the organ to be explored so as to facilitate exploration of the organ.

* * * * *